(12) United States Patent
Jin et al.

(10) Patent No.: US 9,802,977 B2
(45) Date of Patent: Oct. 31, 2017

(54) METHOD OF SYNTHESIZING 25-HYDROXY CHOLESTEROL

(71) Applicants: ZHEJIANG UNIVERSITY OF TECHNOLOGY, Zhejiang (CN); ZHEJIANG GARDEN BIOCHEMICAL HIGH-TECH CO., LTD, Zhejiang (CN); HANGZHOU XIASHA BIOCHEMICAL TECH CO., LTD, Zhejiang (CN)

(72) Inventors: Can Jin, Zhejiang (CN); Weike Su, Zhejiang (CN); Ziqiang Wang, Zhejiang (CN); Jiangang Liu, Zhejiang (CN); Bin Sun, Zhejiang (CN); Wenhao Xu, Zhejiang (CN)

(73) Assignees: ZHEJIANG UNIVERSITY OF TECHNOLOGY, Zhejiang (CN); ZHEJIANG GARDEN BIOCHEMICAL HIGH-TECH CO., LTD, Zhejiang (CN); HANGZHOU XIASHA BIOCHEMICAL TECH CO., LTD, Zhejiang (CN)

( * ) Notice: Subject to any disclaimer, the term of this patent is extended or adjusted under 35 U.S.C. 154(b) by 0 days.

(21) Appl. No.: 15/329,255

(22) PCT Filed: May 22, 2015

(86) PCT No.: PCT/CN2015/079551
§ 371 (c)(1),
(2) Date: Jan. 26, 2017

(87) PCT Pub. No.: WO2016/015512
PCT Pub. Date: Feb. 4, 2016

(65) Prior Publication Data
US 2017/0158729 A1    Jun. 8, 2017

(30) Foreign Application Priority Data
Jul. 30, 2014    (CN) .......................... 2014 1 0368802

(51) Int. Cl.
*C07J 9/00*    (2006.01)

(52) U.S. Cl.
CPC ....................... *C07J 9/00* (2013.01)

(58) Field of Classification Search
CPC .......................................................... C07J 9/00
See application file for complete search history.

(56) References Cited

U.S. PATENT DOCUMENTS 3,868,396 A * 2/1975 Ikekawa ................... C07J 9/00
552/504
4,792,620 A * 12/1988 Paulik .................. B01J 31/0231
560/232

OTHER PUBLICATIONS

Wikipedia, Wikipedia , Tilde, recovered from https://en.wikipedia.org/wiki/Tilde on Mar. 23, 2017, pp. 1-19.*
Norskov et al, Nature Chemistry, Towards the Computational Design of Solid Catalysts, 2009, 1, pp. 37-46.*

* cited by examiner

*Primary Examiner* — Paul A Zucker
(74) *Attorney, Agent, or Firm* — JCIPRNET

(57) ABSTRACT

The present invention discloses a method for synthesizing 25-hydroxy cholesterol. The method is as below: subjecting 24-dehydrocholesterol derivative as a raw material, which undergoes an addition reaction with a hydroxyl containing reagent in an organic solvent under catalysis, and then hydrolyzing the reaction product and separating to obtain 25-hydroxy cholesterol. The present invention adopts hydroxyl containing reagents such as water, formic acid, acetic acid, propionic acid, butyric acid, benzoic acid, p-methyl benzoic acid to replace the commonly used extremely toxic reagents such as Cr reagent, Hg reagent and polyfluorinated acetone in the prior art. The raw materials of the present invention are easily available, and have low effect on environment. The operation and post treatment are convenient. Moreover, the method has the advantages of mild reaction conditions, simple operation, good selectivity, high efficiency, high yield, simple post treatment, easy product separation, less three wastes and easy industrialization.

8 Claims, No Drawings

METHOD OF SYNTHESIZING 25-HYDROXY CHOLESTEROL

CROSS-REFERENCE TO RELATED APPLICATION

This application is a 371 application of an International PCT application serial no. PCT/CN2015/079551, filed on May 22, 2015, which claims the priority benefits of China Application No. 201410368802.8, filed on Jul. 30, 2014. The entirety of each of the above-mentioned patent applications is hereby incorporated by reference herein and made a part of this specification.

BACKGROUND OF THE INVENTION

1. Field of the Invention

The present invention belongs to the technical field of intermediate synthesis, specifically relating to a method for synthesizing 25-hydroxy cholesterol.

2. Description of Related Art 25-hydroxy cholesterol is an important raw material for the synthesis of 25-hydroxy vitamin $D_3$. The 25-hydroxy vitamin $D_3$, also known as calcifediol, is the active metabolite of vitamin $D_3$, has a stronger physiological activity, and does not need to go through the liver metabolism. The 25-hydroxy vitamin $D_3$ not only has all functions of the ordinary vitamin $D_3$, but also has the following unique functions: ① vitamin $D_3$ in some human or animals cannot be directly converted into 25-hydroxy vitamin $D_3$ due to liver function disorder. Even if many vitamins $D_3$ are taken, these vitamins $D_3$ cannot be absorbed. Therefore, 25-hydroxy vitamin $D_3$, as an active substance, bypasses the liver transformation and is directly supplied for human or animals for absorption; ② the 25-hydroxy vitamin $D_3$ in animals can promote the bone development of poultry, maximize the bone mineral density, reduce chick mortality, reduce osteoporosis and cage layer fatigue, improve quality of egg shells, reduce the breakage rate of egg shells, increase the hatching rate and prolong the egg production cycle; ③ compared with vitamin $D_3$, absorption of the 25-hydroxy vitamin $D_3$ is less affected by intestinal damage; and meanwhile, the content of the 25-hydroxy vitamin $D_3$ in plasma is an indicator indicating the nutritional status of vitamin $D_3$.

The 25-hydroxy cholesterol is more difficult in production technique but the market prospect is good and the potential is great. Prior to the present invention, the 25-hydroxy cholesterol is generally prepared by methods such as (a) oxymercuration reduction (Chin. Chem. Lett., 1992, 3, 409), (b) perhydroxytrifluoroacetone hydroxylation (EP594229) or (c) chromium trioxide/acetic anhydride hydroxylation (J. Chem. Research (S), 1999, 708). The reaction formulas are as follows:

(a)

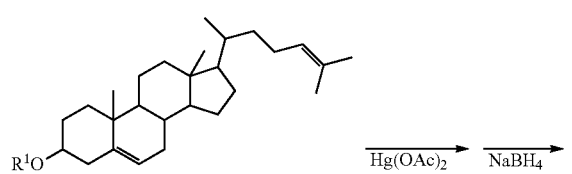

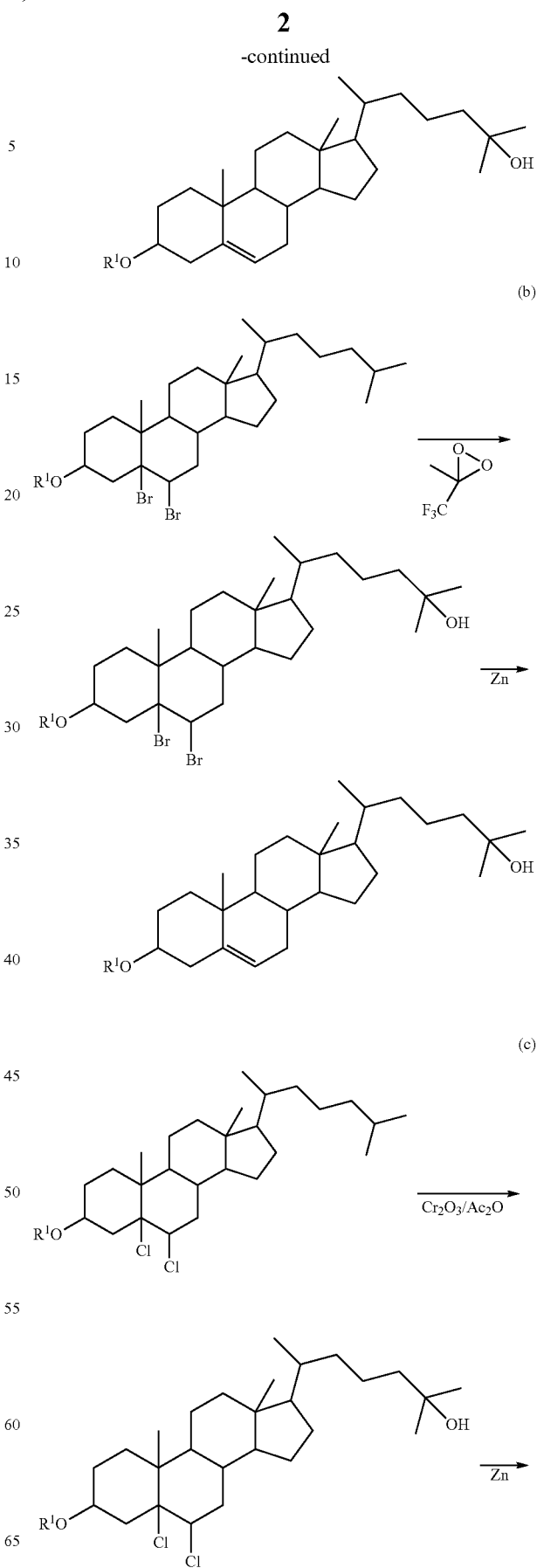

(b)

(c)

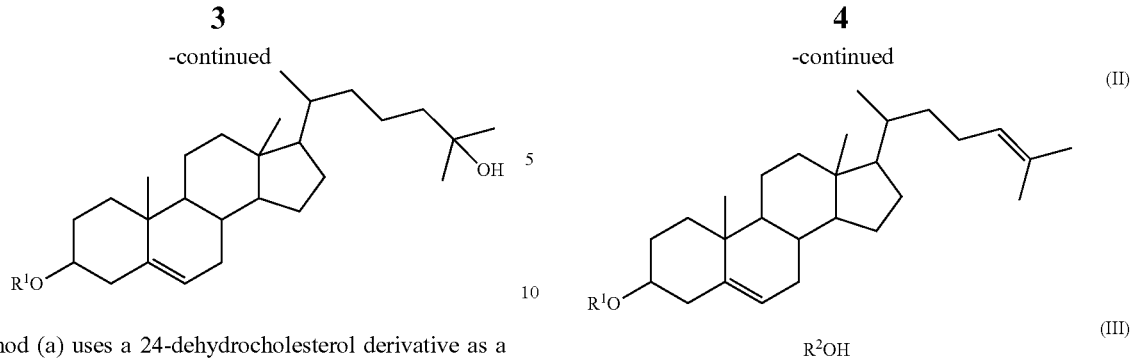

Method (a) uses a 24-dehydrocholesterol derivative as a raw material and uses an extremely toxic Hg reagent, so the operation is unsafe, there are great safety and environmental hazards, the post treatment is troublesome, and Hg is very easy to remain in products and is difficult to remove, the medical standards cannot be reached, and industrialization is difficult.

Method (b) uses a 5,6-dibromo cholesterol derivative as a raw material, and oxidized at the position 25 by perhydroxytrifluoroacetone for preparation, but the trifluoroacetone substance is extremely toxic and may have special toxicity, that is, the substance is teratogenetic, carcinogenic and mutagenic. The method has the disadvantages of high instrument requirements, large operation difficulty, troublesome post treatment, and great safety and environmental hazards.

Method (c) uses a 5,6-dichloro cholesterol derivative as a raw material, oxidized by chromium trioxide, acetic anhydride or trifluoroacetic anhydride and then performs reduction with zinc powder. As the method also uses the heavy metal Cr reagent, the usage amount is too large and post treatment is troublesome, there are great environmental hazards, and industrialization cannot be realized.

Therefore, the development of a method for synthesizing 25-hydroxy cholesterol that is efficient, environmentally friendly and easy for realizing industrialization has high economic and social benefits.

SUMMARY OF THE INVENTION

For the problems existing in the prior art, the present invention is directed to a simple and efficient method for synthesizing 25-hydroxy cholesterol.

The method for synthesizing 25-hydroxy cholesterol is characterized in that: adding a 24-dehydrocholesterol derivative and a hydroxyl containing reagent to an organic solvent and react at −40° C.-150° C. for 1-40 hours in the presence of a catalyst; after completing the reaction, hydrolyzing with alkali, and then separating the reaction solution to obtain 25-hydroxy cholesterol, wherein the structural formulas of the 25-hydroxy cholesterol, the 24-dehydrocholesterol derivative and the hydroxyl containing reagent are shown in formula (I), formula (II) and formula (III) respectively:

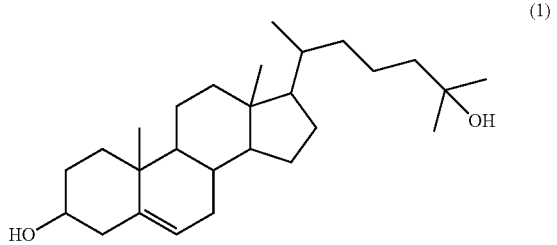

The R1 in formula (II) is the same as the R2 in formula (III), which is H or C1-C12 acyl group.

The method for synthesizing 25-hydroxy cholesterol is characterized in that the amount-of-substance ratio of the 24-dehydrocholesterol derivative to the hydroxyl containing reagent to the catalyst is 1:(1-100):(0.01-1).

The method for synthesizing 25-hydroxy cholesterol is characterized in that the hydroxyl containing reagent is one of water, formic acid, acetic acid, propionic acid, butyric acid, benzoic acid and p-methyl benzoic acid or a mixture thereof at any ratio.

The method for synthesizing 25-hydroxy cholesterol is characterized in that the catalyst is one of sulfuric acid, phosphoric acid, p-toluenesulfonic acid, sodium bisulfate, potassium bisulfate, phosphorus pentoxide, aluminum trichloride, titanium tetrachloride, ferric trichloride, nickel chloride, cobalt chloride, zinc chloride, magnesium chloride, calcium chloride, aluminum tribromide, ferric tribromide, zinc bromide, magnesium bromide, magnesium iodide, scandium trifluoromethanesulfonate, lanthanum trifluoromethanesulfonate, ytterbium trifluoromethanesulfonate, iridium methanesulfonate, neodymium trifluoromethanesulfonate, samarium trifluoromethanesulfonate, zinc trifluoromethanesulfonate, gallium trifluoromethanesulfonate, copper trifluoromethanesulfonate, gold trifluoromethanesulfonate, silver trifluoromethanesulfonate or indium trifluoromethanesulfonate.

The method for synthesizing 25-hydroxy cholesterol is characterized in that the organic solvent is one or a mixture of two or more of toluene, xylene, chlorobenzene, dichloromethane, chloroform, dichloroethane, ethyl acetate, acetone, butanone and cyclohexanone at any ratio.

The method for synthesizing 25-hydroxy cholesterol is characterized in that the reaction temperature is 50° C.-80° C. and the reaction time is 5-8 hours.

The method for synthesizing 25-hydroxy cholesterol is characterized in that the alkali is sodium hydroxide or potassium hydroxide.

The method for synthesizing 25-hydroxy cholesterol is characterized in that the hydrolysis temperature is 50° C.-80° C. and the hydrolysis time is 1-2 hours.

The method for synthesizing 25-hydroxy cholesterol is characterized in that the amount-of-substance ratio of the 24-dehydrocholesterol derivative to the hydroxyl containing reagent to the catalyst is 1:(5-10):(0.01-0.1).

The method for synthesizing 25-hydroxy cholesterol is characterized in that the method is performed based on the following steps: dissolving the 24-dehydrocholesterol derivative in the organic solvent at room temperature; adding the hydroxyl containing reagent and the catalyst; stirring the mixture to react at −40° C.-150° C. for 1-40 hours; after completing the reaction, adding water for layering to remove the aqueous phase; adding aqueous alkali solution to the organic phase to keep the pH of the system at 12; warming the mixture to 50° C.-80° C. and stirring the mixture to react for 1-2 hours; after the reaction, separating liquor to remove the aqueous phase, and washing the organic phase with water again; after drying with anhydrous sodium sulfate, filtering and concentrating to obtain a yellowish crude product; and then re-crystallizing the product with ethyl acetate/petroleum ether to obtain the 25-hydroxy cholesterol.

With the technologies above, the present invention, compared with the prior art, has the following beneficial effects:

The present invention uses a 24-dehydrocholesterol derivative and a hydroxyl containing reagent as raw materials for reaction, and uses the hydroxyl containing reagent to replace the extremely toxic Hg reagent used in the prior art. The hydroxyl containing reagent is easily available, and has little effect on environment. The operation and post treatment are convenient. Moreover, the present invention has the advantages of mild reaction conditions, simple operation, good selectivity, high efficiency, high yield, simple post treatment, easy product separation and easy industrialization.

DESCRIPTION OF THE EMBODIMENTS

The present invention is further described in combination of preferred embodiments, but the protection scope of the present invention is not limited to these embodiments only:

Embodiment 1

4.27 g (10 mmol) of 24-dehydrocholesterol acetate is dissolved in 20 mL of toluene at room temperature (20-25° C.); 6.01 g (100 mmol) of acetic acid and 49.2 mg (0.1 mmol) of scandium trifluoromethanesulfonate (Sc(OTf)$_3$) are added; the mixture is warmed to 50° C. and stirred to react for 5 hours; after TLC tracks the completion of the reaction, 10 mL of water is added to remove the aqueous phase; aqueous sodium hydroxide solution is added to the organic phase; the pH of the system is kept not less than 12; and the system is warmed to 50° C., and stirring is performed for one hour. After TLC detects the finish of the reaction, liquor is separated to remove the aqueous phase; the organic phase is washed with 10 mL of water for layering; after drying the organic phase with anhydrous sodium sulfate, filtering and concentrating are performed to obtain a yellowish crude product; the crude product is re-crystallized with 20 mL of ethyl acetate/petroleum ether (v/v=2:3) to obtain 3.45 g of 25-hydroxy cholesterol with yield of 85.6% and melting point of 179.4-180.8° C., $^1$HNMR (CDCl$_3$, 400 MHz): δ 5.34 (m, 1H, 6-CH), 3.51 (m, 1H, 3-CH), 2.27 (m, 2H), 1.99 (m, 2H), 1.83 (m, 3H), 1.22-1.69 (m, 18H), 1.21 (s, 6H, 26- and 27-CH$_3$), 1.06-1.16 (m, 4H), 1.00 (s, 3H, 19-CH$_3$), 0.93 (d, 3H, 21-CH$_3$), 0.68 (s, 3H, 18-CH$_3$); MS-EI: 402.

In the above embodiment, when acetic acid as the hydroxyl containing reagent is replaced with one of water, formic acid, acetic acid, propionic acid, butyric acid, benzoic acid and p-methyl benzoic acid or a mixture thereof at any ratio, scandium trifluoromethanesulfonate, as the catalyst, is replaced with sulfuric acid, phosphoric acid, p-toluenesulfonic acid, sodium bisulfate, potassium bisulfate, phosphorus pentoxide, aluminum trichloride, titanium tetrachloride, ferric trichloride, nickel chloride, cobalt chloride, zinc chloride, magnesium chloride, calcium chloride, aluminum tribromide, ferric tribromide, zinc bromide, magnesium bromide, magnesium iodide, lanthanum trifluoromethanesulfonate, ytterbium trifluoromethanesulfonate, iridium methanesulfonate, neodymium trifluoromethanesulfonate, samarium trifluoromethanesulfonate, zinc trifluoromethanesulfonate, gallium trifluoromethanesulfonate, copper trifluoromethanesulfonate, gold trifluoromethanesulfonate, silver trifluoromethanesulfonate or indium trifluoromethanesulfonate, and toluene, as the organic solvent, is replaced with one or a mixture of two or more of xylene, chlorobenzene, dichloromethane, chloroform, dichloroethane, ethyl acetate, acetone, butanone and cyclohexanone at any ratio, the same technical effects can be obtained.

Embodiment 2

3.84 g (10 mmol) of 24-dehydrocholesterol is dissolved in 20 mL of chloroform at room temperature (20-25° C.); 6.01 g (100 mmol) of acetic acid, 0.14 g (1 mmol) of aluminum trichloride and 0.1 g of concentrated hydrochloric acid are added; the mixture is warmed to 60° C. and stirred to react for 8 hours; after TLC tracks the completion of the reaction, 10 mL of water is added to remove the aqueous phase; aqueous sodium hydroxide solution is added to the organic phase; the pH of the system is kept not less than 12; and the system is warmed to 50° C., and stirring is performed for one hour. After TLC detects the finish of the reaction, liquor is separated to remove the aqueous phase; the organic phase is washed with 10 mL of water for layering; after drying the organic phase with anhydrous sodium sulfate, filtering and concentrating are performed to obtain a yellowish crude product; the crude product is re-crystallized with 20 mL of ethyl acetate/petroleum ether (v/v=2:3) to obtain 3.24 g of 25-hydroxy cholesterol with yield of 80.5% and melting point of 179.0-180.5° C.

Embodiment 3

4.88 g (10 mmol) of 24-dehydrocholesterol benzoate is dissolved in 30 mL of xylene at room temperature (20-25° C.); 12.20 g (100 mmol) of benzoic acid and 34.6 mg (0.1 mmol) of gold trifluoromethanesulfonate (AuOTf) are added; the mixture is warmed to 80° C. and stirred to react for 8 hours; after TLC tracks the completion of the reaction, 10 mL of water is added to remove the aqueous phase; aqueous sodium hydroxide solution is added to the organic phase; the pH of the system is kept not less than 13; and the system is warmed to 80° C., and stirring is performed to react for one hour. After TLC detects the finish of the reaction, liquor is separated to remove the aqueous phase; the organic phase is washed with 10 mL of water for layering; after drying the organic phase with anhydrous sodium sulfate, filtering and concentrating are performed to obtain a yellowish crude product; the crude product is re-crystallized with 20 mL of ethyl acetate/petroleum ether (v/v=2:3) to obtain 2.95 g of 25-hydroxy cholesterol with yield of 73.4% and melting point of 179.1-180.9° C.

Embodiment 4

The amount-of-substance ratio of the 24-dehydrocholesterol propionate to the mixture of formic acid and acetic acid at a ratio of 1:1 to the phosphoric acid is 1:100:1, other operations are the same as those in embodiment 1, and 3.50 g of 25-hydroxy cholesterol with yield of 87.1% is obtained.

Embodiment 5

The amount-of-substance ratio of the 24-dehydrocholesterol caproate to benzoic acid to magnesium bromide is 1:1:0.01, other operations are the same as those in embodiment 1, and 1.50 g of 25-hydroxy cholesterol with yield of 37.1% is obtained.

Embodiment 6

The catalyst is changed into sodium bisulfate with usage amount of 1 mmol, other operations are the same as those in embodiment 1, and 2.21 g of 25-hydroxy cholesterol with yield of 55% is obtained.

Embodiment 7

The catalyst is changed into zinc bromide with usage amount of 0.5 mmol, other operations are the same as those in embodiment 1, and 3.33 g of 25-hydroxy cholesterol with yield of 82.8% is obtained.

Embodiment 8

The catalyst is changed into cobalt chloride with usage amount of 2 mmol, other operations are the same as those in embodiment 1, and 2.51 g of 25-hydroxy cholesterol with yield of 62.4% is obtained.

Embodiment 9

The catalyst is changed into ferric trichloride with usage amount of 1 mmol, other operations are the same as those in embodiment 1, and 3.16 g of 25-hydroxy cholesterol with yield of 78.6% is obtained.

Embodiment 10

The catalyst is changed into indium trifluoromethanesulfonate with usage amount of 0.2 mmol, other operations are the same as those in embodiment 1, and 3.39 g of 25-hydroxy cholesterol with yield of 84.3% is obtained.

Embodiment 11

The reaction temperature is −40° C., the solvent is changed into dichloromethane, other operations are the same as those in embodiment 1, and 1.71 g of 25-hydroxy cholesterol with yield of 42.7% is obtained.

Embodiment 12

The reaction temperature is 150° C., the solvent is changed into cyclohexanone, other operations are the same as those in embodiment 1, and 1.56 g of 25-hydroxy cholesterol with yield of 38.8% is obtained.

Embodiment 13

The alkali is changed into potassium hydroxide, other operations are the same as those in embodiment 1, and 3.44 g of 25-hydroxy cholesterol with yield of 85.6% is obtained.

What is claimed is:
1. A method for synthesizing 25-hydroxy cholesterol, comprising: adding a 24-dehydrocholesterol derivative and a hydroxyl containing reagent to an organic solvent and react at −40° C.-150° C. for 1-40 hours in the presence of a catalyst; after completing the reaction, hydrolyzing with alkali, and then separating the reaction solution to obtain 25-hydroxy cholesterol, wherein the structural formulas of the 25-hydroxy cholesterol, the 24-dehydrocholesterol derivative and the hydroxyl containing reagent are shown in formula (I), formula (II) and formula (III) respectively:

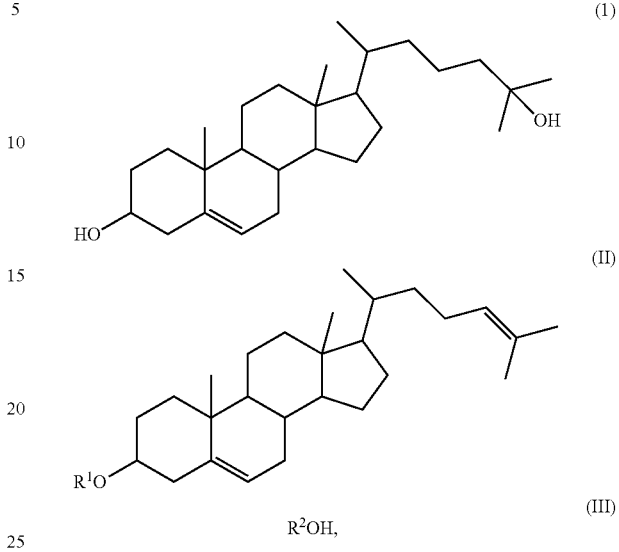

the R1 in formula (II) is the same as the R2 in formula (III), which is H or C1-C12 acyl group,
wherein the hydroxyl containing reagent is one of water, formic acid, acetic acid, propionic acid, butyric acid, benzoic acid and p-methyl benzoic acid or a mixture thereof at any ratio,
wherein the catalyst is one of sulfuric acid, phosphoric acid, p-toluenesulfonic acid, sodium bisulfate, potassium bisulfate, phosphorus pentoxide, aluminum trichloride, titanium tetrachloride, ferric trichloride, nickel chloride, cobalt chloride, zinc chloride, magnesium chloride, calcium chloride, aluminum tribromide, ferric tribromide, zinc bromide, magnesium bromide, magnesium iodide, scandium trifluoromethanesulfonate, lanthanum trifluoromethanesulfonate, ytterbium trifluoromethanesulfonate, iridium methanesulfonate, neodymium trifluoromethanesulfonate, samarium trifluoromethanesulfonate, zinc trifluoromethanesulfonate, gallium trifluoromethanesulfonate, copper trifluoromethanesulfonate, gold trifluoromethanesulfonate, silver trifluoromethanesulfonate or indium trifluoromethanesulfonate.

2. The method for synthesizing 25-hydroxy cholesterol according to claim 1, wherein the mole ratio of the 24-dehydrocholesterol derivative to the hydroxyl containing reagent to the catalyst is 1:(1-100):(0.01-1).

3. The method for synthesizing 25-hydroxy cholesterol according to claim 1, wherein the organic solvent is one or a mixture of two or more of toluene, xylene, chlorobenzene, dichloromethane, chloroform, dichloroethane, ethyl acetate, acetone, butanone and cyclohexanone at any ratio.

4. The method for synthesizing 25-hydroxy cholesterol according to claim 1, wherein the reaction temperature is 50° C.-80° C. and the reaction time is 5-8 hours.

5. The method for synthesizing 25-hydroxy cholesterol according to claim 1, wherein the alkali is sodium hydroxide or potassium hydroxide.

6. The method for synthesizing 25-hydroxy cholesterol according to claim 1, wherein the hydrolysis temperature is 50° C.-80° C. and the hydrolysis time is 1-2 hours.

7. The method for synthesizing 25-hydroxy cholesterol according to claim 1, wherein the mole ratio of the 24-dehydrocholesterol derivative to the hydroxyl containing reagent to the catalyst is 1:(5-10):(0.01-0.1).

8. The method for synthesizing 25-hydroxy cholesterol according to claim 1, wherein the method is performed based on the following steps: dissolving the 24-dehydrocholesterol derivative in the organic solvent at room temperature; adding the hydroxyl containing reagent and the catalyst; stirring the mixture to react at −40° C.-150° C. for 1-40 hours; after completing the reaction, adding water for layering to remove the aqueous phase; adding aqueous alkali solution to the organic phase to keep the pH of the system at 12; warming the mixture to 50° C.-80° C. and stirring the mixture to react for 1-2 hours; after the reaction, separating the mixture to remove the aqueous phase, and washing the organic phase with water again; after drying with anhydrous sodium sulfate, filtering and concentrating to obtain a yellowish crude product; and then re-crystallizing the product with ethyl acetate/petroleum ether to obtain the 25-hydroxy cholesterol.

\* \* \* \* \*